US005912126A

United States Patent [19]
Darzynkiewicz et al.

[11] Patent Number: 5,912,126
[45] Date of Patent: Jun. 15, 1999

[54] METHODS FOR LABELING DNA ENDS WITH HALOGENATED NUCLEOTIDES AND DETECTING SAME WITH ANTIBODIES

[76] Inventors: Zbigniew Darzynkiewicz, 37 Meadow La., Chappaqua, N.Y. 10514; Xun Li, 1635 Morningview Dr., Yorktown Heights, N.Y. 10598; Frank Traganos, 301 66th St., New York, N.Y. 10021

[21] Appl. No.: 08/727,509

[22] PCT Filed: Aug. 28, 1996

[86] PCT No.: PCT/US96/14250

§ 371 Date: Oct. 22, 1996

§ 102(e) Date: Oct. 22, 1996

[87] PCT Pub. No.: WO97/08345

PCT Pub. Date: Mar. 6, 1997

Related U.S. Application Data

[60] Provisional application No. 60/002,963, Aug. 30, 1995.

[51] Int. Cl.$^6$ .................................................. C12Q 1/68
[52] U.S. Cl. .............................................. 435/6; 536/24.3
[58] Field of Search ................................. 435/6, 7.1, 345, 435/333, 91.1; 530/388.1, 387; 436/546, 63, 64, 545, 56, 94; 536/24.3–24.33, 26.6; 424/85.8; 250/339.07, 370.11; 513/93, 47; 73/61.72

[56] References Cited

U.S. PATENT DOCUMENTS

| | | | |
|---|---|---|---|
| 4,780,406 | 10/1988 | Dolbear et al. | 435/6 |
| 4,851,331 | 7/1989 | Vary et al. | 435/6 |
| 5,360,893 | 11/1994 | Owens et al. | 530/350 |
| 5,399,586 | 3/1995 | Davies et al. | 514/488 |
| 5,436,134 | 7/1995 | Haugland et al. | 435/34 |
| 5,464,833 | 11/1995 | Nakai et al. | 514/251 |
| 5,464,871 | 11/1995 | Kun et al. | 514/617 |
| 5,476,659 | 12/1995 | Goodman et al. | 424/278.1 |
| 5,519,053 | 5/1996 | Kun et al. | 514/457 |
| 5,527,682 | 6/1996 | Owens | 435/6 |
| 5,539,094 | 7/1996 | Reed et al. | 536/23.5 |

OTHER PUBLICATIONS

Szabo, "Overall Changes in Chromatin Sensitivity to DNase 1 during Differentiation," Experimental Cell Research 169 (1987), pp. 158–168.

Gratzner, H.G.:Monoclonal Antibody to 5–Bromand 5–iododeoxyuridine. A New Reagent for Detection of DNA replication in *Science*. 218:474–475, 1982.

Dolbeare, F., H.G. Gratzner, M.G. Pallavicine and J.W. Gray.:Flow Cytometric Measurement of Total DNA Content and Incorporated Bromodeoxyuridine in *Proc Natl Acad Sci USA*. 80:5573–5577, 1983.

Begg, A.C., N.J. Menally, D.C. Shrieve and H. Karchner.: A Method to Measure the Duration of DNA Synthesis and the Potential Doubling Time from a Single Sample in *Cytometry*. 6:620–626, 1985.

Falini, B., S. Canino, S. Sacchi, C. Ciani, M.F. Martelli, J. Gerdes, H. Stein, S. Pileri, M. Gobbi, Fagioli, O. Minelli and L. Flenghi.:Immunocytochemical Evaluation of the Percentage of Proliferating Cells in Pathalogical Bone Marrow and Peripheral Blood Samples with the Ki–67 and Anti–Bromodeoxyuridine Antibodies in *Br J. Hematol*. 69:311–320, 1988.

Williamson K., I. Halliday, P. Hamilton, J. Rudell, M. Varma, P. Maxwell, A. Crockard and B. Rowland.:In Vitro BrdUrd Incorporation of Colorecttal Tumor Tissue in *Cell Prolif*. 26:115–124, 1983.

deFazio, A. and M.H.N. Tattersall.:Rapid Fluorometric Detection of Drug Resistant Tumor Cells in *Br J Cancer*. 52:633–636, 1985.

Takagi S., M.L. McFadden, R.E. Humphreys, B.A. Woda and T. Sairenji.:Detection of 5–Bromo–2–Deoxyuridine (BrdUrd) Incorporation with Monoclonal Anti–BrdUrd Antibody After Deoxyribinuclease Treatment in *Cytometry*. 14:640–648, 1993.

Latt, S.A.:Detection of DNA Synthesis in Interphase Nuclei by Fluorescence Microscopy in *J. Cell Biol*. 62:546–560, 1974.

Darzynkiewicz, Z., F. Traganos and M. Melamed.:Distinction Betwen 5–Bromodeoxyuridine Labeled and Unlabeled Mitotic Cells by Flow Cytometry in *Cytometry*. 3:345–348, 1983.

Poot, M., M. Kubbies, H. Hoehn, A. Grossman, Y. Chen and P. Rabinovitch.:Cell Cycle Analysis Using Continuous Bromodeoxyuridine Labeling and Hoechst 33258–Ethidium Bromide Bivariate Floe Cytometry in *Meth Cell Biol*. 33:185–198, 1990.

Hutchinson, F.:The Lesions Produced by Ultraviolet Light in DNA Containing 5–Bromouracil in *Quart Rev Biophy*. 6:201–246, 1973.

Zwanenburg. T.S.B., A.A. van Zeeland and A.T. Natarajan.: Influence of Incorporated Broxodeoxyuridine on the Induction of Chromosomal Alterations by Ionizing Radiation and Long Wave UV in CHO Cells in *Mutation Res*. 150:283–292, 1985.

(List continued on next page.)

*Primary Examiner*—Kenneth R. Horlick
*Assistant Examiner*—Jeffrey Siew

[57] ABSTRACT

The invention pertains to the field of DNA detection for basic research, medical diagnostic testing, and forensic testing. Methods are provided for end labeling of DNA strands without a denaturation step so that cellular morphology can be better preserved. The DNA strands are first incubated with a halogenated deoxynucleotide triphosphate, such as brominated deoxyuridine triphosphate (BrdUTP), and an enzyme which can catalyze the addition of the halogenated deoxynucleotide to the 3' OH ends of the DNA strand, such as terminal deoxynucleotidyl transferase (TdT). The resulting modified DNA strands are then incubated with a labeled antibody, such as a fluoresceinated monoclonal antibody, that binds specifically to the halogenated deoxynucleotide. The label is then detected, e.g., by flow cytometry. The methods have utility in detecting apotosis, DNA synthesis and/or repair, and as general methods for end labeling DNA.

20 Claims, 4 Drawing Sheets

OTHER PUBLICATIONS

Gorczyca, W., S. Bruno, R.J. Darzynkiexicz, J. Gong and Z. Darzynkiewicz.:DNA Strand Breaks Occuring During Apoptosis:Their Early in Situ Detection by the Terminal Deoynucleotidyl Transferase and Nick Translation Assays and Prevention by Serine Protease Inhibitors in *Int. J. Oncol.* 1:639–648, 1992.

Gorczycz, W., J. Gong and Z. Darzynkiewicz.:Detection of DNA Strand Breaks in Individual Apoptotic Cells by the In Situ Terminal Deoxynucleotidyl Transferase and Nick Translation Assays in *Cancer Res.* 53:1945–1951, 1993.

Darzynkiewicz, Z., S. Bruno, G. Del Bino, W. Gorczyca, M.A. Hotz, P. Lossota and F. Traganos.: Features of Apoptotic Cells Measured by Flow Cytometry in *Cytometry.* 13:795–808, 1992.

Gong, J., F. Traganos and Z. Darzynkiewicz.:A Selective Procedure for DNA Extraction from Apoptotic Cells Applicable for Gel Electrophoresis and Flow Cytometry in *Anal Biochem* (in press).

Li, X., R. Patel, M.R. Melamed and Z. Darzynkiewicz.:The Cell Cycle Effects and Induction of Apoptosis by 5–Bomouridine in Cultures of Human Leukemic MOLT–4 and HL–60 Cell Lines and Mitogen Stimulated Norrmal Lymphocytes in *Cell Prolif* (in press).

Bino, G.D., J.S. Skierski and Z. Darzynkiewicz.:The Concentration–Dependent Diversity of Effects of DNA Topoisomerase I and II Inhibitors on the Cell Cycle of HL–60 Cells in *Experimental Cell Research.* 195:485–491, 1991.

Bruno, S. and Z. Darzynkiewicz.:Cell Cycle Dependent Expression and Stability of the Nuclear Protein Detected by Ki–67 Antibody in HL–60 Cells in *Cell Prolif.* 25:31–40, 1992.

Bruno , S., G.D. Bino, P. Lassota, W. Giaretti and Z. Darzynkiewicz.:Inhibitors of Proteases Prevent Endonucleolysis Accompanying Apoptotic Death of HL–60 Leukemic Cells Normal Thymocytes in *Leukemia.* 6(11), 1113–1120, (Nov.) 1992.

Compton, M.M.:A Biochemical Hallmark of Apoptosis:Internucleosomal Degradation of the Genome in *Cancer and Metastasis Reviews.* 11:105–119, 1992.

Chapman, R.S., C.M. Chresta, A.A. Herberg, H.M. Beere, S. Heer, A.D. Whetton, J.A. Hickman and C. Dive.:Further Characterisation of the In Situ Terminal Deoxynucleotidyl Transfferase (TdT) Assay for the Flow Cytometric Analysis of Apoptosis in Drug Resistant and Drug Sensitive Leukaemic Cells in *Cytometry.* 20:245–256, 1995.

Darzynkiewicz, Z., S. Bruno, G.D. Bino, W. Gorczyca, M.R. Hotz, P. Lassota and F. Traganos.:Features of Apoptotic Cells Measured by Flow Cytometry in *Cytometry.* 13:795–808, 1992.

Darzynkiewicz, Z.:Apoptosis in Antitumor Stratedies-:Modulation of Cell Cycle or Differentiation in *Journal of Cellular Biochemistry.* 56:1–9, 1994.

Dive, C.C.D. Gregory, D.J. Phipps, D.L. Evans, A.E. Milner and A.H. Wyllie.:Analysis and Discrimination of Necrosis and Apoptosis (Programmed Cell Death) By Multiparameter Flow Cytometry in *Biochimica et Biophysica Actta.* 1133:275–285, 1992.

Dolbeare, F. and J.R. Selden.:Immunochemical Quantitation of Bromodeoxyuridine:Application to Cell–Cycle Kinetics in *Methods In Cell Biology.* 41:297–316, 1994.

Gavrieli, Y., Y. Sherman and S.A. Ben–Sasson.:Indentification of Programmed Cell Death In Situ via Specific Labeling of Nuclear DNA Fragmentation in *The Jornal of Cell Biology.* 119(3):493–501, (Nov.) 1992.

Gold, R., M. Schmied, G. Rothe, H. Zischler, H. Breitschopf, H. Wekerle and H. Lassmann.:Detection of DNA Fragmentation in Apoptosis:Application of In Situ Nick Translation to Cell Culture Systems and Tissue Sections in *The Journal of Histochemistry and Cytochemistry.* 41(7):1023–1030, 1993.

Gorczyca, W., K. Bigman, A. Mittelman, T. Ahmed, J. Gong, M.R. Melamed and Z. Darzynkiewicz.:Induction of DNA Strand Breaks Associates with Apoptosis during Treatment of Leukemias in *Leukemia.* 7(5):659–670, (May) 1993.

Hotz, M.A., F. Traganos and Z. Darzynkiewicz.:Changes in Nuclear Chromatin Related to Apoptosis or Necorosis Induced by the DNA Topoisomerase II Inhibitor Fostriecin in MOLT–4 and HL–60 Cells Are Revealed by Alered DNA Sensitivity to Denaturation in *Experimental Cell Research.* 201, 184–191, 1992.

Kamentsky, L.A. and L.D. Kamentsky.:Microscope–Based Multiparameter Laser Scanning Cytometer Yielding Data Comparable to FLow Cytometry Data in *Cytometry.* 12:381–387, 1991.

Koopman, G., C.P.M. Reutelingsperger, G.A.M. Kuijten, R.M.J. Keehnen, S.T. Pais and M.H.J. van Oers.:Annexin V for Flow Cytometric Detection of Phosphatidylserine Expression on B Cells Undergoing Apoptosis in *Blood.* 84(5):1415–11420, (Sep. 1) 1994.

Li, Xun, F. Traganos, M.R. Melamed and Z. Darzynkiewicz.:Detection of 5–Bromo–2–Deoxyuridine Incorporated into DNA by Labeling Strand Breaks Induced by Photolysis (SBIP) in *International Journal of Oncology.* 4:1157–1161, 1994.

Li, X., F. Traganos and Z. Darzynkiewicz.:Simultaneous Analysis o DNA Replication and Apoptosis during Treatment of HL–60 Cells with Camptothecin and Hyperthermia and Mitogen Stimulation of Human Lymphocyte in *Cancer Research.* 54:4289–4293, (Aug.) 1994.

Li, X. G. Jianping, E. Feldman, K. Seiter, F. Traganos and Z. Darzynkiewicz.:Apoptotic Cell Death During Treatment of Leukemias in *Leukemia and Lymphoma.* 13(1):65–70, 1994.

Li, X., F. Traganos, M.R. Melamed and Z. Darzynkiewicz.:Single–Step Procedure for Labeling DNA Strand Breaks with Fluorescein–or BODIPY–Conjugated Deoxynucleotides:Detection of Apoptosis and Bromodeoxyuridine Incorrporation in *Cytometry.* 20:172–180, 1995.

Nicoletti, I., G. Migliorati, M.C. Pagliacci, F. Grignani and C. Riccardi.:A Rapid and Simple Method for Measuring Thymocytte Apoptosis by Propidium Iodide Staining and Flow Cytometry in *Journal of Immnological Methods,* 139:271–279, 1991.

Raza, A., S. Gezer, S. Mundle, X.Z. Gao, S. Alvi, R. Borok, S. Rifkin, A. Iftikhar, V. Shetty, A. Parcharidou, J. Loew, B. Marcus, Z. Khan, C. Chaney, J. Showel, S. Gregory and H. Preisler.:Apoptosis in Bone Marrow Biopsy Samples Involving Stromal amd Hematopoietic Cells in 50 Patients with Myelodysplastic Syndromes in *Blood*, 86(1):268–276, (Jul. 1) 1995.

P.R. Walker, V.M. Weaver, B. Lach, J. LeBlanc and M. Sikorska.:Endonuclease Activities Associates with High Molecular Weight and Internucleosomal DNA Fragmentation in Apoptosis in *Experimental Cell Research.* 213:100–106, 1994.

Wijsman, J. H., R.R. Jonker, R. Keijzer, C.J.H. Van De Velde, C.J. Cornelisse and J.H. Van Dierendonck.:A New Method to Detect Apoptosis in Paraffin Sections:In Situ End–Labeling of Fragmented DNA in *The Journal of Histochemistry and Cytochemistry*. 41(1):7–12, 1993.

Jirkowski, G.F., J.F. Ramalho–Ortigao, T. Lindl and H. Seliger.:Immunocytochemistry of 5–bromo–2'deoxyuridine labelled oligonucleotide probes in *Histo Chemistry*. 91(1):51–53, 1989.

Jirikowski, G.F., J.F. Ramalho–Ortigao, K.W. Kesse and F.E. Bloom:In Situ Hybridization of Semithin Epon Sections with:BrdU Labelled Oligonucleotide Probes in *Histo Chemistry*. 94(1):187–190, 1990.

Bayer, J.A., P. DeVries, H. Herweijer and J.G.J. Bauman.:The use of *E. Coli* exonuclease III to generate single stranded DNA in BrdUrd cell–cycle analysis permits simultaneous detection of cell surface antigens in *Journal of Immunological Methods*. 132:13–24, 1990.

Beisker, W. and W.N. Hittelman.:Measurement of the Kinetics of DNA Repair Synthesis after UV Irradiation Using Immunochemical Staining of Incorporated 5–Bromo–2'–deoxyuridine and Flow Cytometry in *Experimental Cell Research*. 174:156–167, 1988.

Glickman, B.W.:The Role of DNA Polmerase I In Pyrimidine Dimer Excision and Repair Replication in *Escherichia Coli* K12 Following Ultraviolet Irradation in *Boichimica et Biophysica Acta*. 335:115–122, 1974.

Southern, E.M.:Detection of Specific Sequences Among DNA Fragments Separated by Gel Electrophoresis in *J. Mol. Biol.*. 98:503–517, 1975.

Zucker, M.L. and W.H. Prusoff.:Effect of Incorporation of 5–Iodo–2'–Deoxyuridine into HSV–1 DNA on Virion Sensitivity to Ultraviolet Light in *Biochemical Pharmacology*. 36(20):3741–3476, 1987.

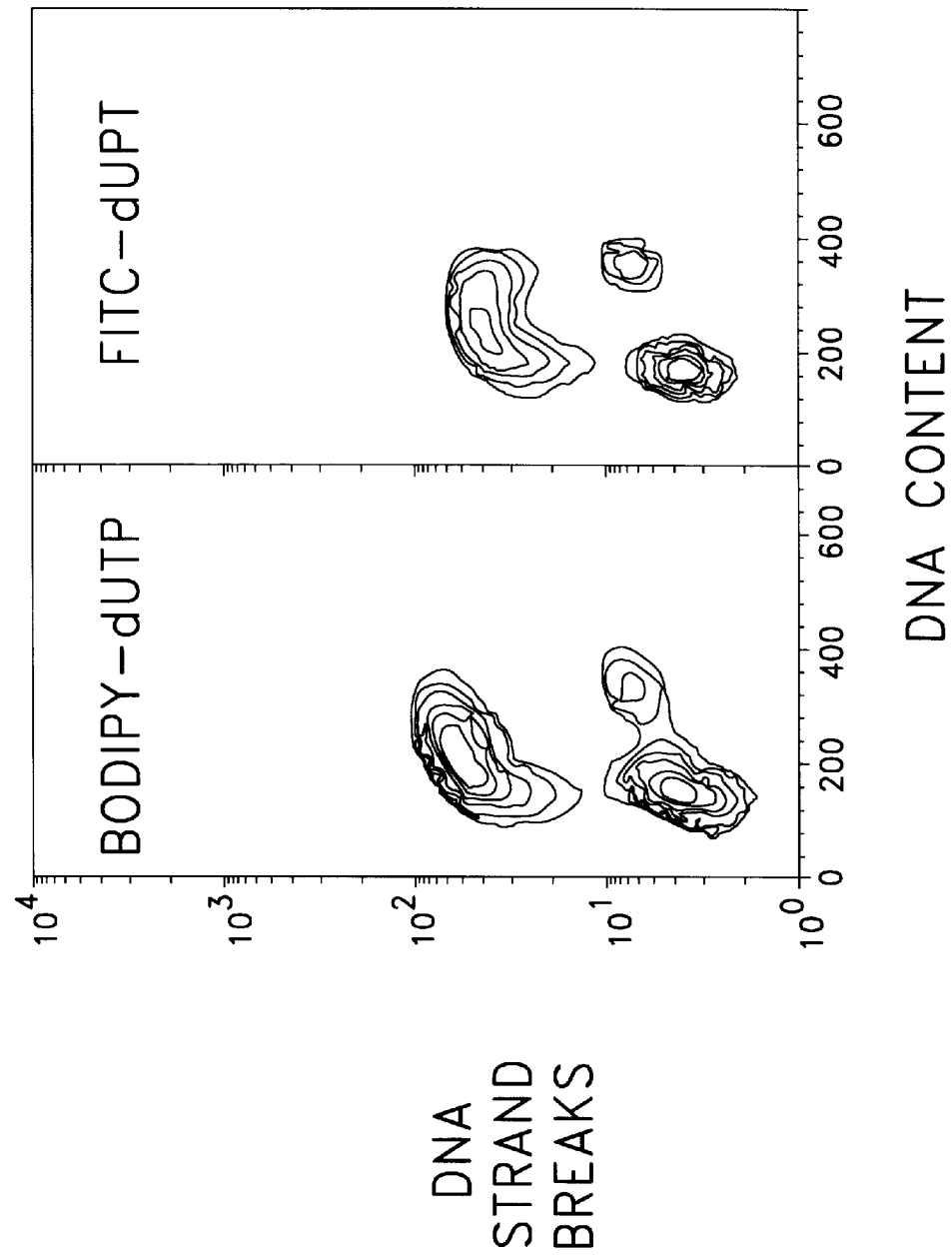

METHODS FOR LABELING DNA ENDS WITH HALOGENATED NUCLEOTIDES AND DETECTING SAME WITH ANTIBODIES

This application claims priority to U.S. Provisional Application Ser. No. 60/002,963, filed Aug. 30, 1995, which is incorporated herein in its entirety by reference.

This invention was made with United States government support under grant R01 28704 awarded by the National Cancer Institute. The United States government has certain rights in the invention.

TECHNICAL FIELD

The present invention relates to the field of DNA detection for basic research, medical diagnostic testing, and forensic testing. More specifically, the invention relates to methods of detecting DNA by attaching labeling groups to the ends of DNA strands, and then detecting the labeling groups by using antibodies specific for those labeling groups to attach a secondary label that can be observed, for example, by eye or by a fluorescence or spectrophotometric detector.

The present invention has particular utility in detecting the occurrence of programmed cell death, which is known as "apoptosis." It also has utility as a method for detecting DNA replication and repair, and as a general method for DNA end labeling.

BACKGROUND ART

There is currently considerable interest in the process of programmed cell death, known as "apoptosis." This process is considered to be a normal part of an organism's biological defense system. For example, when cells become infected with certain viruses, the resulting overstimulation of the cellular machinery appears to trigger apoptosis; the infected cells die, and thus protect the remaining cells from infection. It is also believed that apoptosis is an important weapon in the body's defense against cancerous growths, and that cancer results at least in part from a loss of the ability of affected cells to trigger their own death.

Researchers often wish to determine whether cells have died because of apoptosis, or because of some other cause. This is generally determined by examining the DNA of the cells. The DNA of cells that have died from apoptosis is typically broken into quite small and uniquely sized fragments, which is generally not the case when cells die from other causes. The DNA fragmentation that is characteristic of apoptosis is caused by enzymes in the cells known as endonucleases, and results in fragments of approximately 300 kilobases and 50 kilobases in length. Often, breaks in the DNA occur in sections between the nucleosome proteins, leading to broken pieces of DNA 180–200 base pairs long (Arends, Morris & Wyllie 1990, Compton 1992, Oberhammer et al. 1993, Walker et al. 1994, Wyllie, Kerr & Curie 1980).

To determine whether apoptosis has occurred, the DNA strand breaks need to be labeled in some manner so that they can be detected. Cell samples are generally first fixed with a crosslinking fixative, so that the small fragments of DNA are not lost from the sample cells in subsequent washing steps. The cells are then treated to make them permeable to further reagents. In two prior art methods, the permeabilized cells are then reacted with deoxynucleotides that have been labeled with either biotin or digoxygenin, using the enzymes DNA polymerase (the "nick translation" enzyme) or terminal deoxynucleotidyl transferase (TdT) to attach the labeled nucleotides to the 3'OH ends of the DNA fragments (Darzynkiewicz et al. 1992, Gorczyca et al. 1992; Gavrieli et al. 1992, Gorczyca, Gong & Darzynkiewicz 1993, Wijksman et al. 1993). The biotin or digoxygenin nucleotides themselves are not readily detectable; however, biotin can be specifically bound by the lectin avidin, and antibodies that can specifically bind digoxygenin are also available. By binding avidin or digoxygenin antibodies to the fluorescent compound fluorescein, which can be done by reacting them with fluorescein-5-isothiocyanate (FITC), and then using these as secondary labels, the DNA strand breaks can be visualized by observing the fluorescence of the labeled DNA strand ends. A single step method utilizing deoxynucleotides directly labeled with fluorochromes, which is simpler but less sensitive than the above-described indirect methodology, has also been recently described (Gold et al. 1993, Li, et al. 1995).

Another area of active research is the study of DNA replication and repair. One method for detecting the cellular replication and/or repair of DNA is known as Strand Breaks Induced by Photolysis, or SBIP. In this method, the living cells are first supplied with halogenated DNA precursors such as BrdUrd or IdUrd, which the cells will incorporate into the DNA during replication or repair. The cells are then exposed to ultraviolet light, which causes the DNA to break where the halogenated precursors have been incorporated. The resulting DNA strand breaks can then be detected by fluorochrome labeled antibodies, as described above (Li, Traganos & Darzynkiewicz, 1994, Li et al. 1994c, 1995).

A third important use for DNA strand labeling is perhaps the oldest and most widely practiced; end-labeling of DNA strands during the purification and characterization of DNA, so that the DNA can be detected. As well appreciated by those in the field, DNA research samples are generally too small even to be seen with the naked eye. In order to detect them, they are often "end labeled" at a very early stage of purification. For example, it is common to end label DNA with nucleotides containing radioactive phosphorous ($P^{32}$); the presence of the DNA can then be detected at various stages of analysis using a geiger counter, by scintillation counting or by autoradiography. However, such methods are currently being phased out due to the biological hazards involved in working with radioactive compounds, and because of the ecological problems caused by the need to dispose of such radioactive materials. These methods are being replaced largely by methods that provide for labeling with fluorescent compounds. However, methods in use prior to the present invention are often complex, and are generally somewhat expensive.

SUMMARY OF THE INVENTION

Each of the above-described prior art methods for DNA end labeling suffer from important limitations. The most important limitations are that the prior art methods are only moderately sensitive, and that they require the use of relatively expensive reagents. Such limitations are especially problematic when large numbers of DNA samples must be routinely analyzed, such as in medical diagnostic testing.

Upon reviewing the prices charged by vendors offering halogenated and fluorescein-labeled nucleotides, we noticed that the compound bromodeoxyuridine triphosphate, or "BrdUTP", costs only about one tenth of one percent as much as equivalent amounts of digoxygenin-, biotin-, or fluorochrome-conjugated deoxynucleotides. Our subsequent research showed that BrdUTP could be incorporated at the 3'OH ends of DNA at least as efficiently as directly labeled or digoxigenin or biotin labeled dUTP. We also discovered that strands of DNA into which the BrdUTP was incorporated could be readily detected by anti-BrdUrd antibodies which had been fluorescently labeled; anti-BrdUrd antibody is a widely available reagent, which is commonly used to detect the uptake of brominated uridine (BrdUrd) from culture media by living cells, as a measure of cell proliferation (Dolbeare & Selden 1994, Gratzner 1982). These two discoveries led to the present invention. The invention can be summarized as the enzymatic incorporation of halogenated deoxynucleotide triphosphates onto the 3'OH ends of DNA strands, followed by the detection of the incorporated halogenated nucleotides using antibodies. Because of the low cost and general availability of reagents, this invention offers an attractive alternative to a variety of DNA end labeling methods currently in use. Surprisingly, this effective and inexpensive approach has heretofore been completely overlooked. We have also found that the sensitivity of BrdUTP detection is significantly higher than that of either biotin- or digoxygenin conjugated dUTP, which was quite unexpected. Of course, as will be readily appreciated by those of ordinary skill in the art, other halogenated deoxynucleotide triphosphates can be used in the present invention as well.

Accordingly, it is an object of the present invention to provide a simple and inexpensive method for the end-labeling of DNA strands.

It is a further object of the present invention to provide a method for the detection of DNA strands that is more sensitive than methods using either biotin or digoxygenin conjugated deoxynucleotides, and much more sensitive than direct labeling methods.

It is another object of the invention to provide an inexpensive yet sensitive method for the detection of apoptosis.

It is a further object of the invention to provide inexpensive yet sensitive methods for the detection of DNA replication and/or repair.

The objects of the invention that are recited above, as well as numerous other objects of the present invention, can be more readily understood from the following detailed description.

BRIEF DESCRIPTION OF DRAWINGS

FIG. 1a and 1b show isometric contour maps of DNA content versus DNA strand break labeling for apoptotic cells; the left-hand panel of FIG. 1a shows the label achieved by the present invention which is contrasted with labeling produced by two alternative methods; FIG. 1b shows labeling produced by two additional alternative methods;

FIG. 2 shows flow cytometry measurements of the results obtained by using the method of the present invention to detect strand breaks that were induced by ultraviolet irradiation of DNA containing BrdUrd incorporated during the process of DNA synthesis; panel labeled "BrdUTP" shows the results with the present invention; panel labeled "d-dUTP" shows the results of the prior art technique of incorporating digoxigenin-labeled nucleotides; panel labeled "b-UTP" shows the results of the prior art technique of incorporating biotinylated nucleotides; panel labeled "BODIPY-dUTP" shows the results of incorporating nucleotides directly labeled with the fluorescent dye BODIPY.

FIG. 3 the same experiment as shown in FIG. 2 measured by a Laser Scanning Cytometer.

MODES FOR CARRYING OUT THE INVENTION

Figure 1A:
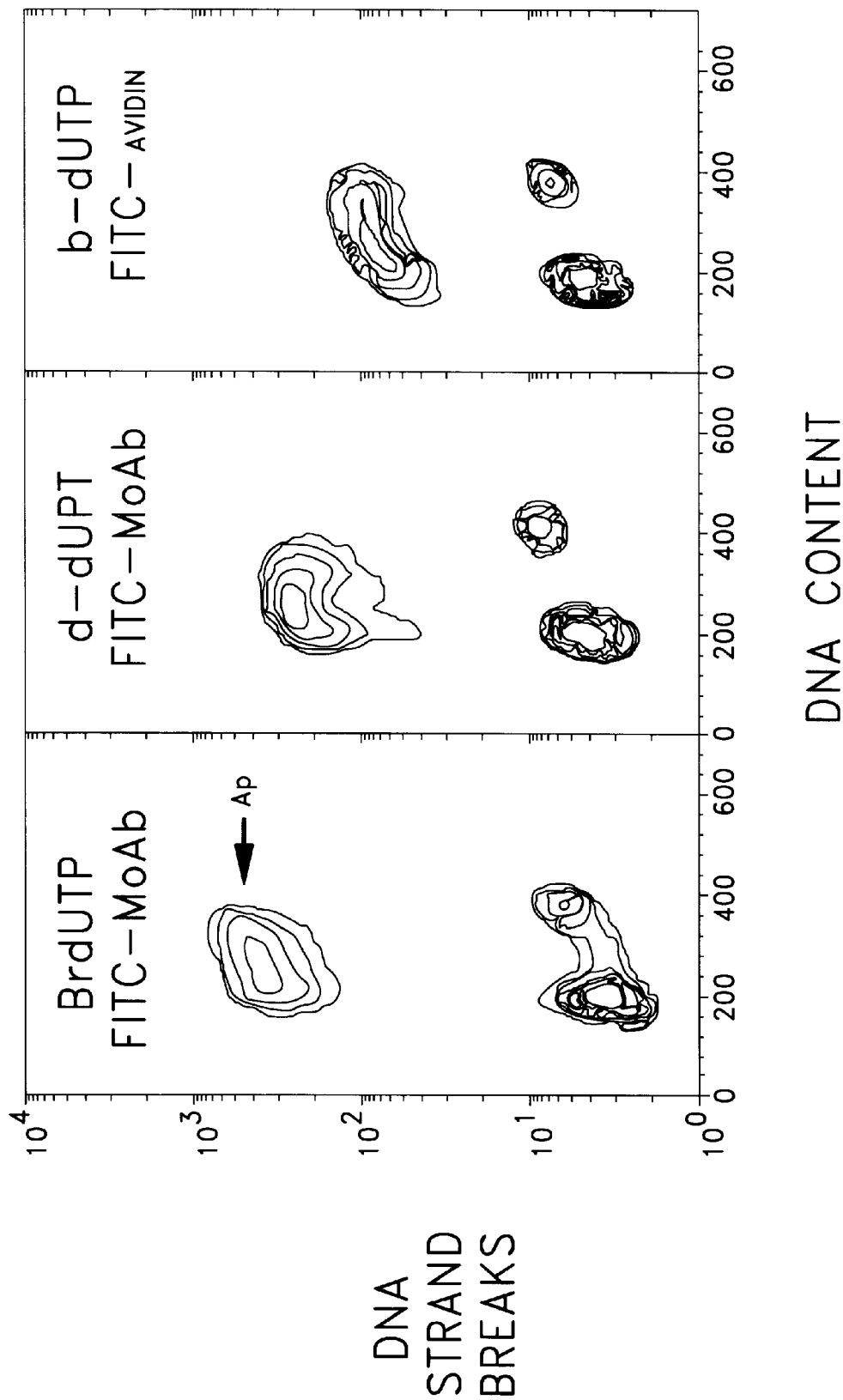

The methods of the present invention are quite straightforward both in design and in practice. Those of ordinary skill in the field of DNA labeling will readily appreciate that the primary requirements of the present invention are the use of a halogenated deoxynucleotide triphosphate, in conjunction with an enzyme that will attach the halogenated nucleotide to the 3'OH ends of DNA strands. For example, terminal deoxynucleotidyl transferase (TdT) or a DNA polymerase could be used for this purpose. Then, an antibody that specifically binds to the halogenated nucleotide, and which has itself been labeled with one or more detectable group, is added. The antibody binds to the brominated nucleotide, and the presence and/or location of the labeled antibody indicates the presence and/or location of the DNA.

In the examples provided herein, brominated deoxyuridine triphosphate (BrdUTP) has been used to label DNA strands by the methods of the present invention. However, as will be readily appreciated by those of ordinary skill in the field of DNA labeling, other halogenated deoxynucleotide triphosphates and corresponding antibodies can be substituted for BrdUTP and anti-BrdUrd antibodies. For example, bromo deoxyadenosine triphosphate (BrdATP) and anti-brominated adenosine antibodies may be used in the present method, as could iododeoxyuridine triphosphate (IdUTP) and anti-iodinated deoxyuridine antibodies. Various other nucleotide and antibody combinations can also be used, as will be appreciated by those in the field. Of course, it is important that the labeled antibodies used be specific for the particular halogenated nucleotide. Thus, it is expected, for example, that when iodinated uridine triphosphate is attached to the 3'OH ends of the DNA strands, an antibody that specifically binds to iodouridine should be used. Of course, it is often possible to take advantage of cross-reactivity; some antibodies against halogenated nucleotides are known to show some cross-reactivity with nucleotides bearing a different halogen (Dolbeare & Selden 1994). For example, antibodies against iodinated deoxyuridine (IdUrd) can also react with brominated deoxyuridine (BrdUrd), and thus might be used to detect either one (although the affinity for IdUrd is higher).

In the examples given below, fluorescent monoclonal antibodies are used. However, the use of polyclonal antibodies is also within the scope of the present invention. In addition, it is not necessary that fluorescence be used as the detectable label. Those of ordinary skill in the art will readily appreciate that a wide spectrum of detectable labels have been used in biochemistry, and that any of them could be used in the present invention. For example, a radioactive moiety could alternatively be used, and such a moiety might either be contained within the structure of the nucleoside, or could be an added radioactive group. There are a variety of other detectable labels that can be attached to antibodies—spin labels, chromophores, enzymes, enzyme-linked chromophoric systems, etc.—and the use of such alternate labels would be well within the scope of the present invention.

The enzymatic addition of the halogenated deoxynucleotide in the methods of the present invention can be carried out using a variety of enzymes. The enzyme used must accept deoxynucleotide triphosphates and DNA strands as substrates; and must catalytically attach the deoxynucleotide to the DNA strand. As will be appreciated by those in the field, there are two well known enzymes that meet these requirements. One is terminal deoxynucleotide transferase (TdT), and the other is DNA polymerase. Various forms of these enzymes, for example, from different source organisms, may be available, and all would be expected to be suitable for use in the present invention. However, it is not intended that the present invention be limited to the use of these enzymes, as any other enzyme having the aforementioned activity would also be suitable for use in the present invention. For example, there may be enzymes having that activity that are not presently known, but the use of those enzymes in the methods described herein would be well within the scope of the present invention.

It is expected that the methods of the present invention will generally result in the attachment of more than one halogenated nucleotide to each DNA strand. This multiple labeling provides certain advantages; it allows for the attachment of several antibody molecules per DNA strand, which we believe is at least in part responsible for the high sensitivity of the methods described. However, multiple labeling is not necessary to the present invention, and the addition of only a single halogenated nucleotide to each DNA strand and the subsequent detection of same using labeled antibodies is well within the scope of the present invention.

In the examples below, only a single halogenated nucleotide triphosphate is used. However, it would be well within the scope of the present invention to use a plurality of different halogenated nucleotide triphosphates in a single reaction, along with a corresponding plurality of labeled antibodies.

As demonstrated in the examples to follow, one advantage of the methods of the present invention is that they are more sensitive than many alternative methods. In many cell systems, DNA degradation during apoptosis is very extensive; in such cases, even the least sensitive methods of DNA strand break labeling may be adequate for detection of apoptotic cells. However, there may be situations when increased sensitivity is needed. For example, the present invention's high sensitivity will be of value in detecting "atypical" apoptosis, which is when the endonucleolyic DNA cleavage stops at 50–300 kD size fragments rather than progressing to the production of smaller fragments (Chapman et al. 1995, Cohen et al. 1992, Collins et al. 1992, Oberhammer et al. 1993). The increased sensitivity of the present invention will also be of value when only very small samples are available for testing. In addition, the increased sensitivity of the present assay will be of value in labeling the relatively few primary DNA strand breaks that can be induced by ionizing radiation, certain antitumor drugs, free radicals, etc., in order to estimate extent of DNA damage. Detecting the incorporation of BrdUrd during DNA repair may also require the more efficient labeling of DNA strand breaks that the present invention provides. Those of ordinary skill in the field will readily appreciate other situations in which the sensitivity of the present methods provides an advantage over alternative methods.

It is not necessary to the present invention that the reason for its superior sensitivity be understood. However, several possible explanations are apparent. One is that incorporation of BrdUTP by TdT is more efficient than incorporation of nucleotides which are conjugated to bulky fluorochromes or to digoxygenin/biotin. Another is that the detection of the incorporated BrdUrd by the antibody may be more efficient e.g. due to greater accessibility of the epitope. A third explanation may be that the number of FITC molecules attached to each molecule of antibody may be higher in the case of BrdUrd monoclonal antibodies than for fluorochrome conjugates.

As mentioned above, another major advantage of BrdUTP over other markers of DNA strand breaks is its low cost. Furthermore, BrdUrd antibodies are already widely used and are available from many sources (Dolbeare & Selden 1994, Gratzner, 1982). Use of BrdUTP for DNA strand break labeling, therefore, is expected to make analysis of apoptosis more widely available, especially in routine clinical testing, when cost of the reagents plays a significant role in testing decisions. For example, preliminary clinical studies suggest that the analysis of tumor cell apoptosis during chemotherapy may provide evidence of drug effectiveness and be an early prognostic marker (Gorczyca et al. 1993a, Li et al. 1994a, Raza et al. 1995), and the availability of the inexpensive, simple methods of the present invention may make such testing more common.

The methods of the present invention can be best understood by reference to the following example experiments carried out using BrdUTP and using fluorescein labeled anti-brominated uridine antibodies for detection. Of course, it is not intended that these experiments limit the scope of the present invention, as many alternatives are possible, as described hereinabove and otherwise, as will be apparent to those of ordinary skill in the art.

GENERAL MATERIALS AND METHODS

Cells

HL-60 human promyelocytic leukemia cells were originally provided by Dr. Harry A. Crissman of the Los Alamos National Laboratory (Los Alamos, N.Mex.). The cells were maintained in RPMI 1640 (GIBCO, Grand Island, N.Y.) supplemented with 10% fetal bovine serum, 100 units/ml of penicillin, 100 $\mu$g/ml of streptomycin, and 2 mM L-glutamine (GIBCO) as previously described (Bruno et al. 1992, Bruno & Darzynkiewicz, 1992). The cells grew exponentially at densities below $5 \times 10^5$ cells per ml.

Induction of Apoptosis

Apoptosis of HL-60 cells was triggered by cells' exposure to DNA topoisomerase I inhibitor camptothecin (CAM) which induces DNA lesions in form of the "cleavable complexes" (Hsiang et al. 1985). It was postulated that collision of DNA replicating forks with such lesions is responsible for cell death (Hsiang, Lihou & Liu, 1989). Indeed, apoptosis of HL-60 cells treated with CAM was shown to be very specific to cells progressing through S phase; cell death occurs rapidly and rather synchronously, affecting almost exclusively a population of S phase cells (FIG. 1, see Del Bino et al. 1991). Exponentially growing HL-60 cells treated with CAM, thus, provide a convenient model to measure particular parameters of apoptotic cells. Populations of apoptotic cells as produced by this method are relatively uniform and can be compared, within the same sample, with the cell population not undergoing apoptosis i.e. with $G_1$ and $G_2$+M cells.

To induce apoptosis, the cells were incubated in the presence of 0. 15 $\mu$M DNA topoisomerase I inhibitor camptothecin (CAM; Sigma) for 3 hours, as described (Del Bino, Skierski & Darzynkiewicz 1991). For subsequent analysis, the cells were fixed in suspension in 1 % methanol-free formaldehyde (Polysciences, Inc., Warrington, Pa.) in Hanks' buffered salt solution (HBSS) for 15 min on ice, then centrifuged, rinsed with HBSS, resuspended in 70% ethanol. Such samples were stored at −20° C. for up to four days.

Fluorescence measurements

Cellular fluorescence was measured using either a FAS-Can flow cytometer (Becton Dickinson) or the multiparameter Laser Scanning Cytometer (LSC; CompuCyte, Inc., Cambridge, Mass., Kamentsky & Kamentsky, 1991). Propidium iodide (PI) was added to each sample; this labels all double stranded DNA with a fluorescent red color, which can be distinguished from the green fluorescence of fluorescein, and serves as a control. The red (PI) and green (FITC, BODIPY) fluorescence from each cell were separated and quantified by FACScan using the standard optics and LYSYS 11 software (Becton Dickinson), as described (Li et al. 1995). Using the LSC, the cells were illuminated with 488 nm wavelength light from the argon ion laser, and the emissions were separated by a 570 nm dichroic mirror. The green (530±20 nm) and red (>610 nm) fluorescence were measured by separate photomultipliers. Cells in $G_2$ phase were discriminated from cell doublets based on the difference in pulse shape. The instrument allows one to measure cells placed on slides, with rates up to 100 cells per sec, with an accuracy comparable to that of flow cytometers (Kamentsky & Kamentsky 1991, Li et al. 1994c, 1995).

Controls

Control samples were analyzed similarly to the various test samples. Controls consisted of cells that were: (1) incubated in absence of BrdUrd; (2) incubated in absence of CAM to induce apoptosis; (3) incubated with the TdT reaction medium minus the TdT enzyme. All experiments were repeated at least 3 times, yielding essentially identical results.

EXAMPLE 1

DNA strand break labeling with BrdUTP

Cells were fixed by suspension in 1 % methanol-free formaldehyde (Polysciences, Inc., Warrington, Pa.) in Hanks' buffered salt solution (HBSS) for 15 min on ice. The cells (approximately $10^6$ per sample) were then rinsed twice with PBS and resuspended in 50 µl of TdT reaction buffer containing all the reagents as described above for the single step procedure, with the exception that instead of a fluorochrome-conjugated dUTP, 0.25 nmoles of BrdUTP (Sigma) was added. Following incubation (60 min at 37° C.) the reaction was stopped by washing the cells twice in 15 mM $Na_2EDTA$-NaOH, pH 7.8. The cells were then incubated in 100 µl of a solution containing 0.7 µg of FITC-conjugated anti-BrdUrd MoAb (Becton Dickinson, San Jose, Calif., clone B44), 0.1 % Triton X-100® (brand of polyoxyethylene surfactant obtained from Sigma); and 1% BSA. The cells were counterstained with 5 µg/ml of PI, in the presence of RNase, as described (Li et al. 1995). Samples were then analyzed by flow cytometry, as described above.

DNA strand break labeling using prior art methods

One step (direct fluorescence) procedure

The direct procedure was primarily used to label DNA strand breaks in apoptotic cells. The fixed cells were rinsed twice with phosphate buffered salt solution (PBS) and incubated in 50 µl of TdT reaction buffer containing: 10 µl of 5× concentrated buffer solution (I M potassium cacodylate; 125 mM Tris-HCI, pH 6.6; 1.26 mg/ml bovine serum albumin, BSA); 5 µl of 25 mM cobalt chloride; 0.5 µl (12.5 units) of TdT (all from Boehringer Mannheim, Indianapolis, IN) and 0.25 nmoles of fluorescinated dUTP (f-dUTP; from Boehringer) or fluoresceinated ATP (f-ATP; Boehringer Mannheim) or BODIPY® conjugated dUTP (B-dUTP; kindly provided by Dr. Richard P. Haugland, Molecular Probes). The volume of the incubation medium was adjusted with distilled water to 50 µl. The cells were incubated with the reaction buffer for 60 min at 37 C, then rinsed twice with 15 mM EDTA (pH 8.0) and once with 0. 1% Triton X-100® (brand of polyoxyethylene surfactant obtained from Sigma); in PBS. The cells were then resuspended in 1 ml of PBS containing 2.5 µg/ml of propidium iodide (PI; Molecular Probes, Inc.) and 0. 1 %. DNase free RNase (Sigma). Samples were analyzed by flow cytometry as described above.

Two-step procedure

This procedure was used to label both the photolysis-induced DNA strand breaks (SBIP) as well as DNA breaks in apoptotic cells. The samples were processed using the TdT (ApopagTag™) kit, kindly provided by ONCOR Inc. (Gaithersburg, Md.), as described before (Li et al. 1994, 1995). Incorporation of digoxygenin conjugated dUTP (d-dUTP) into DNA by this kit is catalyzed by exogenous TdT; the incorporated d-dUTP is then detected with fluorescein labeled digoxygenin antibodies. In parallel experiments, DNA strand breaks were labeled using biotin labeled dUTP (b-dUTP) and fluoresceinated avidin (both from Boehringer Mannheim) as described before (Gorczyca et al. 1992, Li et al. 1993, 1994c). DNA was counterstained with 5 µg/ml of PI, in the presence of RNase, as described (Li et al. 1995). Samples were then analyzed by flow cytometry as described above.

RESULTS

FIG. 1 shows bivariate distributions (isometric contour maps) of DNA content vs. DNA strand break labeling for exponentially growing HL-60 cells incubated for 3 h with 0.15 µM camptothecin which preferentially induces apoptosis (Ap) of cells progressing through S phase (Del Bino et al. 1991). The first panel on the left, labeled "BrdUTP FITCMoAb" shows the results obtained using a method of the present invention, wherein BrdUTP was incorporated at the 3'OH ends of DNA strands by terminal deoxynucleotidyl transferase (TdT), and the incorporated BrdUrd was detected by a fluorescently labeled BrdUrd monoclonal antibody. The arrow labeled "Ap" indicates the localization of cells that have undergone apoptosis. Note the exponential scale of the ordinate. The abscissa is relative DNA content per cell, based upon PI (red) fluorescence. The next two panels represent indirect labeling of DNA strand breaks utilizing prior art methods, wherein DNA strands are labeled by either digoxygenin conjugated dUTP (d-dUTP) or biotinylated dUTP (b-dUTP). The two right panels show cell distributions following a direct, single-step DNA strand break labeling, either with BODIPY or FITC conjugated dUTP; these are also prior art methods. As it is evident, the greatest separation of apoptotic from nonapoptotic cells is achieved following DNA strand break labeling with BrdUTP.

The results shown in FIG. 1 illustrate the differences in discrimination of apoptotic cells when the method of the present invention is used, as compared with several other methods of DNA strand break labeling: the indirect methods, utilizing b-dUTP or d-dUTP followed by FITC /avidin or FITC conjugated to digoxygenin MoAb (ApopTag kit manufactured by ONCOR), and the direct ones utilizing FITC-or BODIPY conjugated dUTP. The data demonstrate that although the direct methods of DNA strand break labeling employing f-dUTP or BODIPY-dUTP provided sufficient separation of the apoptotic from nonapoptotic cell populations (over eight-fold difference in fluorescence intensity), the DNA strand break associated fluorescence was significantly higher in the case of indirect labeling. Thus, the difference in fluorescence intensity between apoptotic and nonapoptotic ($G_1$) cells ("signal to noise ratio" in detecting apoptosis) was over 20- and over 37-fold for b-dUTP (followed by FITC/avidin) and d-dUTP (followed by FITC/digoxygenin MoAb), which is over twice and over fourfold higher, respectively, compared to f-dUTP.

These quantitative differences between the various methods are further illustrated in Table 1. In this table, the relative fluorescence intensity of apoptotic cells is expressed as a ratio of the mean fluorescence intensity of the labeled apoptotic population to the mean fluorescence intensity of the nonapoptotic cells (Ap vs.G, cell populations). The mean values (+/−SD) of several (n=4–10) estimates of this ratio for each method, obtained in separate experiments, are given. For comparison, the apoptosis labeling index represents the differences normalized with respect to the direct procedure employing FITC-dUTP.

TABLE 1

Differences in fluorescence intensity of apoptotic cells following DNA strand break labeling with different methods.

| Method, Fluorochrome | Relative Fluorescence Intensity | Apoptosis Labeling Index |
| --- | --- | --- |
| Direct, FITC-dUTP | 8.4 ± 0.4 | 1 |
| Direct, BODIPY-dUTP | 10.0 ± 1.7 | 1.2 |
| Indirect, biotin-dUTP FITC/avidin | 20.7 ± 3.4 | 2.5 |
| Indirect, digoxygenin-dUTP, FITC/MoAb | 37.3 ± 2.1 | 4.4 |
| Indirect, BrdUTP FITC/MoAb | 72.0 ± 15.3 | 8.6 |

Surprisingly, the difference in intensity of DNA strand break labeling-associated fluorescence between apoptotic and nonapoptotic cell populations was highest in the case of labeling with BrdUTP. The "signal to noise ratio" provided by this method of DNA strand break labeling was over 70-fold, which was more than eight-fold better compared with the direct labeling methods and nearly twice as good as that offered by the most sensitive indirect assay, namely the one based on d-dUTP incorporation.

EXAMPLE 2

Induction of DNA strand breaks in BrdUrd-labeled cells by UV illumination (SBIP)

To label DNA replicating cells, BrdUrd (Sigma Chemical Co., St. Louis Mo.) was added to cultures at a concentration of 20 µM, for 40 min. For analysis of BrdUrd incorporation using the SBIP method, the cells incubated with this precursor were treated with 2% dimethyl sulfoxide (DMSO; Sigma) and 20 µg/ml of Hoechst 33258 (Molecular Probes, Inc., Eugene, Oreg.) for additional 20 min. The cells were then centrifuged, resuspended in 2 ml of ice cold HBSS, and the cell suspensions were transferred into 60×15 mm polystyrene Petri dishes (Corning, N.Y.). The dishes were then placed directly on the glass surface of a Fotodyne UV 300 analytic DNA transilluminator, containing four 15 watt bulbs (Fotodyne Inc., New Berlin, Wis.) providing maximal illumination at 300 nm wavelength, as described before (Li et al. 1994b, 1994c. 1995). The cells were exposed to UV light for 5 min; exposure to UV light photolyses the DNA; i.e., induces DNA strand breaks at the sites of BrdUrd incorporation (Li et al., 1994(c)). The average intensity of UV light at the surface on which the cells were exposed, measured by a UVX-25 sensor (UVP, Inc.,Upland, Calif.), was 4.5 mW/cm$^2$. The cells were then centrifuged, suspended in HBSS, fixed in suspension in 100% methanol on ice, and stored in methanol at minus 20° C. for up to four days.

Labeling of DNA Strand Breaks with BrdUTP

Figure 2A:
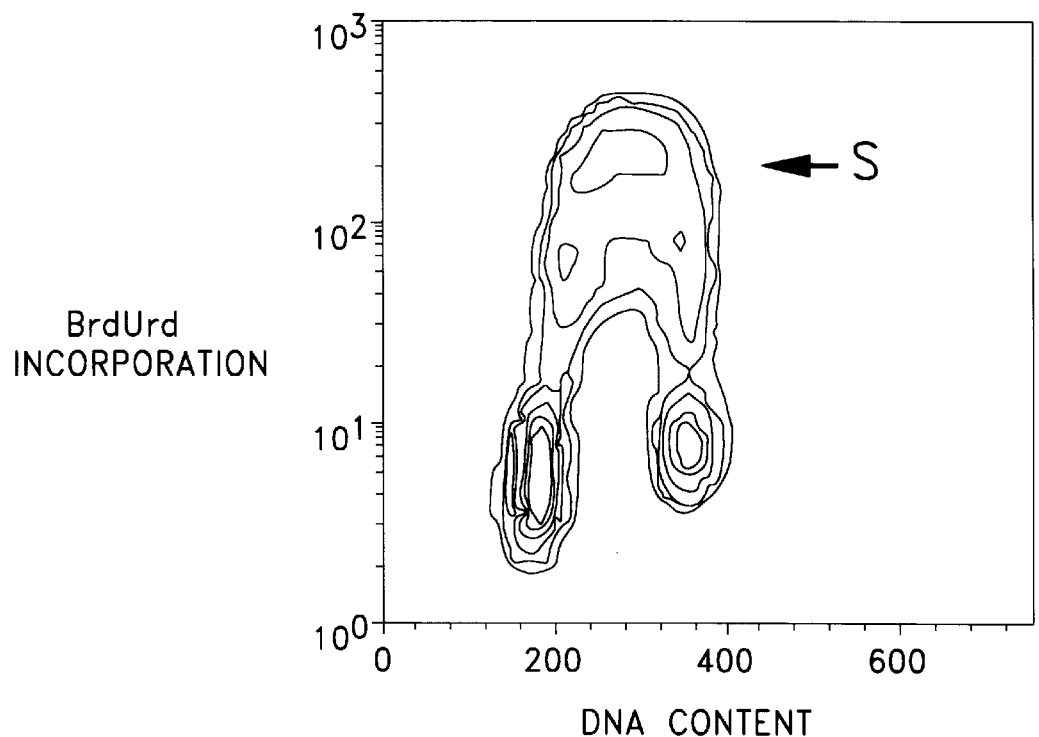
FIG. 2a shows results following ultraviolet irradiation.
Figure 2B:
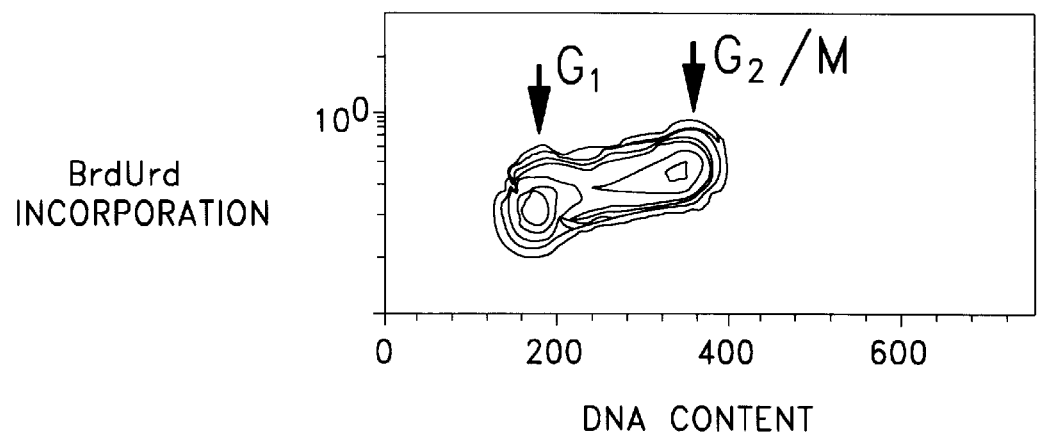
FIG. 2b shows results from cells that received no ultraviolet irradiation.
Figure 3A:
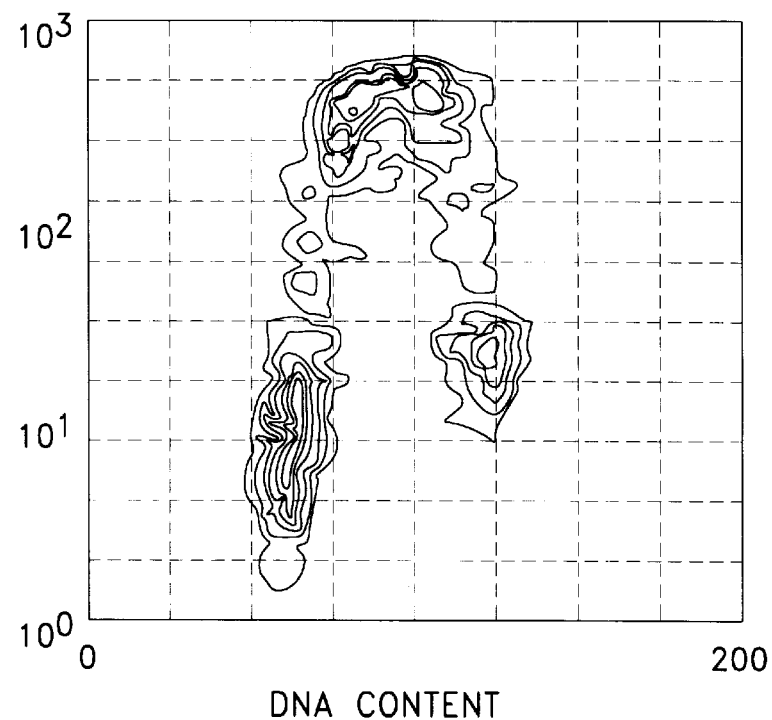
FIG. 3a shows results following ultraviolet irradiation.
Figure 3B:
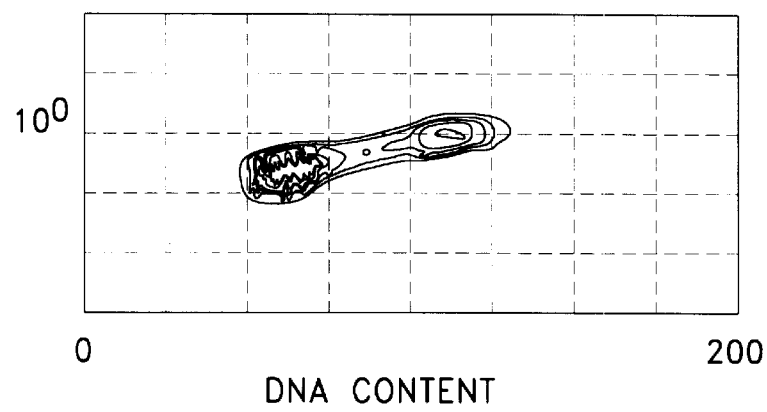
FIG. 3b shows results from cells that received no ultraviolet irradiation.

DNA strand breaks were then labeled with BrdUTP followed by labeling with anti-ErdUrd monoclonal antibody conjugated to FITC, as described in Example 1 above. PI was also added to label DNA as a measure of DNA content, as described above. The treated cells were then either measured by flow cytometry (FIGS. 2a and 2b) or by the Laser Scanning Cytometer (LSC, CompuCyte, Inc.) (FIGS. 3a and 3b), as also described above.

RESULTS

The results are shown in FIG. 2. The two left panels show the results obtained using flow cytometry; the two right panels show the results obtained using the Laser Scanning Cytometer. Both methods gave acceptable results. The two bottom panels represent cells that were not exposed to UV light; note that apparently no break sites were introduced. It should be noted that without the step of DNA denaturation (which requires cell treatment with strong acids or heating; Dolbeare et al. 1983, Dolbeare & Selden, 1994), BrdUrd incorporated during DNA replication was undetected by the monoclonal antibody used. This was evident from the fact that no labeling was observed when the photolysis step was omitted (FIG. 2, bottom panels).

IDUSTRIAL APPLICABILITY

The present invention has industrial applicability in the fields of scientific research, diagnostic medicine, forensic medicine. More specifically, the invention can be used by researchers to label DNA in the course of, for example, genetic research. It can also be used by diagnostic laboratories wishing to test patient samples, for example, to determine if cells have undergone apoptosis. The invention can also be used in forensic medicine, for example, to end label DNA fragments used in restriction fragment lenght polymorphism (RFLP) analysis to determine the origin of crime scene samples. A wide spectrum of other industrial applications will be readily apparent to those of skill in the art.

REFERENCES

The references cited herein are incorporated by reference in their entirety:

ARENDS, M. J., MORRIS R. G., WYLLIE A. H. (1990) Apoptosis: The role of endonuclease. Am. J. Pathol. 136, 593.

BRUNO S., DARZYNKIEWICZ Z. (1992) Cell cycle dependent expression and stability of the nuclear protein detected by Ki67 antibody in HL-60 cells. Cell Prolif. 25, 31.

BRUNO, S. DEL BINO G., LASSOTA P., GIARETTI W., DARZYNKIEWICZ Z. (1992) Inhibitors of proteases prevent endonucleolysis accompanying apoptotic death of HL-60 leukemic cells and normal thymocytes. Leukemia 6, 1113.

CHAPMAN R. S., CHRESTA C. M., HERBERG A. A. et al. (1995) Further characterization of the in situ terminal deoxynucleotidyl transferase (TdT) assay for the flow cytometric analysis of apoptosis in drug resistant and sensitive leukaemic cells. Cytometry 20, 245.

COHEN G. M., SUN X., SNOWDEN R. T., DINSDALE D., SKILLETER D. N. (1992) Key morphological features of apoptosis may occur in the absence of internucleosomal fragmentation. Biochem. J. 286, 331.

COLLINS R. J., HARMON B. V., GOBE G. C., KERR J. F. R. (1992)

Internucleosomal DNA cleavage should not be the sole criterion for identifying apoptosis. *Int. J. Rad. Biol.* 61, 451.

COMPTON M. M. (1992) A biochemical hallmark of apoptosis: Internucleosomal degradation of the genome. *Cancer Metast. Rev.* 11, 105.

DARZYNKEEWICZ Z., BRUNO S., DEL BINO G., GORCZYCA W., HOTZ M. A., LASSOTA P., TRAGANOS F. (1992) Features of apoptotic cells measured by flow cytometry. *Cytometry* 13, 795.

DEL BINO G., SKIERSKI J., DARZ C. Z. Z. (1991) The concentration-dependent diversity of effects of DNA topoisomerase I and II inhibitors on the cell cycle of HL-60 cells. *Exp. Cell Res.* 195, 485.

DOLBEARE F., GRATZNER H. G., PALLAVICINI M. G., GRAY J. W. (1983) Flow cytometric measurement of total DNA content and incorporated bromodeoxyuridine. *Proc. Natl. Acad. Sci. USA* 80, 5573.

DOLBEARE F., SELDEN J. R. (1994) Immunochemical quantitation of bromodeoxyuridine: Application to cell cycle kinetics. *Meth. Cell Biol.* 41, 297.

GAVRIELI Y., SHERMAN Y., BEN-SASSON S. A. (1992) Identification of programmed cell death in situ via specific labeling of nuclear DNA fragmentation. *J. Cell Biol.* 119, 493.

GOLD R., SCHMIED M., ROTHE G., ZIECHLER H., BREITSCHOPF H., WEKERLE H., LASSMAN H. (1993) Detection of DNA fragmentation in apoptosis: Application of in situ nick translation to cell culture systems and tissue sections. *J. Histochem. Cytochem.* 41, 1023.

GORCZYCA W., BRUNO S., DARZYNKIEWICZ R. J., GONG J., DARZYNKIEWICZ Z. (1992) DNA strand breaks occurring during apoptosis: Their early in situ detection by the terminal deoxynucleotidyl transferase and nick translation assays and prevention by serine protease inhibitors. *Int. J. Oncol.* 1, 639.

GORCZYCA W., BIGMAN K., MITTELMAN A. et al. (1993a) Induction of DNA strand breaks associated with apoptosis during treatment of leukemias. *Leukemia* 7, 659.

GORCZYCA W., GONG J., DARZYNKIEWICZ Z. (1993) Detection of DNA strand breaks in individual apoptotic cells by the in situ terminal deoxynucleotidyl transferase and nick translation assays. *Cancer Res.* 52, 1945, 1993.

GRATZNER H. G. (1982) Monoclonal antibody to 5-bromodeoxyuridine. A new reagent for detection of DNA replication. *Science* 218, 474.

HSIANG Y-H., HERTZBERG R., HECHT S LIU L.F. (1985) Camptothecin induces protein-linked DNA breaks via mammalian DNA topoisomerase 1. *J. Biol. Chem.* 260, 14873.

HSIANG Y-H., LIHOU M. G., LIU L. F. (1989) Arrest of replication forks by drug-stabilized topoisomemw I DNA cleavable complexes as a mechanism of cell killing by camptothecin. *Cancer Res.* 49, 5077.

KAMENTSKY L. A., KAMENTSKY L. D. (1991). Microscope-based multiparameter laser scanning cytometer yielding data comparable to flow cytometric data. *Biometry* 12, 381.

LI X., GONG J., FELDMAN E., SEITER K., TRAGANOS F., DARZYNKIEWICZ Z. (1994a) Apoptotic cell death during treatment of leukemias. *Leukemia and Lymphoma* 13, 65.

LI X., TRAGANOS F., DARZYNKIEWICZ Z. (1994b) Simultaneous analysis of DNA replication and apoptosis during treatment of HL-60 cells with camptothecin and hyperthermia and mitogen stimulation of human lymphocytes. *Cancer Res.* 54, 4289.

LI X., TRAGANOS F., MELAMED M.R., DARZYNKIEWICZ Z. (1994c) Detection of 5-bromo-2deoxyuridine incorporated into DNA by labeling strand breaks induced by photolysis (SBIP). *Int. J. Oncol.* 4, 1157.

LI X., TRAGANOS F., MELAMED M.R., DARZYNKIEWICZ Z. (1995) Singlestep procedure for labeling DNA strand breaks with fluorescein- or BODIPY-conjugated deoxynucleotides: Detection of apoptosis and bromodeoxyuridine incorporation. *Cytometry,* 20, 172.

OBERHAMMER F., WILSON J. W., DIVE C. et al. (1993) Apoptotic death in epithelial cells: Cleavage of DNA to 300 and 50 kb fragments prior to or in the absence of internucleosomal degradation of DNA. *EMB J.* 12, 3679.

RAZA A., GEZER S., MUNDLE S. et al. (1995) Apoptosis in bone marrow biopsy samples involving stromal and hematopoetic cells in 50 patients with myelodystrophic syndromes. *Blood* 86, 268.

WALKER R., WEAVER V. M., LACH B., SIKORSKA M. (1994) Endonuclease activities associated with high molecular weight and internucleosomal DNA fragmentation in apoptosis. *Exp. Cell Res.* 213, 100.

WIJSMAN J. H., JONKER R. R., KEIJZER R., VAN DE VELDE C. J. H., CORNELISSE C. J., VAN DIERENDONCK JH (1993) A new method to detect apoptosis in paraffin sections: In situ end-labeling of fragmented DNA. *J. Histochem. Cytochem.* 41, 7.

WYLLIE A. H., KERR J. F. R., CURRIE A. R. (1980) Cell death: The significance of apoptosis. In: Bourne G. H., Danielli F. J. and Jeon K. W. (eds), International Review of Cytology, Vol. 68, Academic Press, New York, N.Y., pp. 251–306.

We claim:

1. A method for labeling nuclear DNA strands within a cell, comprising the steps of:

a. incubating said cell containing said DNA strands with a halogenated deoxynucleotide triphosphate (HdNTP) and an enzyme that catalytically attaches the halogenated deoxynucleotide (HdN) of said HdNTP onto the 3'OH ends of said DNA strands; and b. reacting the resulting HDN-DNA strands without denaturation of the DNA with a labeled anti-halogenated deoxynucleotide (anti-HdN) antibody which specifically binds to said HdN.

2. The method of claim 1 wherein said halogenated deoxynucleotide triphosphate is selected from the group consisting of brominated deoxyadenosine triphosphate; brominated deoxycytosine triphosphate; brominated deoxyguanosine triphosphate; brominated deoxyuridine tripho sphate; brominated deoxythymidine triphosphate; iodinated deoxyadenosine triphosphate; iodinated deoxycytosine triphosphate; iodinated deoxyguanosine triphosphate; iodinated deoxyuridine triphosphate; and iodinated deoxythymidine triphosphate.

3. The method of claim 1 wherein said enzyme is selected from the group consisting of terminal deoxynucleotidyl transferase (TdT) and DNA polymerase.

4. The method of claim 1 wherein said labeled anti-halogenated nucleotide (anti-HdN) antibody is selected from the group consisting of fluorescently labeled anti-HdN monoclonal antibody; radiolabeled anti-HdN monoclonal antibody; peroxidase-labeled anti-HdN monoclonal antibody; chromophore labeled anti-HdN monoclonal antibody; fluorescently labeled anti-HdN polyclonal antibody; radiolabeled anti-HdN polyclonal antibody; peroxidase-labeled anti-HdN polyclonal antibody; and chromophore labeled anti-HdN polyclonal antibody.

5. A method for labeling nuclear DNA strands within a cell, comprising the steps of:
   a. incubating said cell containing said DNA strands with brominated deoxynucleotide triphosphate (BrdNTP) and an enzyme that catalytically attaches the brominated deoxynucleotide (BrdN) of said BrdNTP onto the 3'OH ends of said DNA strands; and
   b. reacting the resulting BrdN-DNA strands without denaturation of the DNA with a labeled anti-brominated deoxynucleotide (anti-BrdN) antibody which specifically binds to said BrdN.

6. The method of claim 5 wherein said brominated deoxynucleotide triphosphate is selected from the group consisting of brominated deoxyadenosine triphosphate; brominated deoxycytosine triphosphate; brominated deoxyguanosine triphosphate; brominated deoxyuridine triphosphate; and brominated deoxythymidine triphosphate.

7. The method of claim 5 wherein said enzyme is selected from the group consisting of terminal deoxynucleotidyl transferase (TdT) and DNA polymerase.

8. The method of claim 5 wherein said labeled anti-brominated nucleotide (anti-BrdN) antibody is selected from the group consisting of fluorescently labeled anti-BrdN monoclonal antibody; radiolabeled anti-BrdN monoclonal antibody; peroxidase-labeled anti-BrdN monoclonal antibody; chromophore labeled anti-BrdN monoclonal antibody; fluorescently labeled anti-BrdN polyclonal antibody; radiolabeled anti-BrdN polyclonal antibody; peroxidase-labeled anti-BrdN polyclonal antibody; and chromophore labeled anti-BrdN polyclonal antibody.

9. A method for labeling nuclear DNA strands within a cell, comprising the steps of:
   a. incubating said cell containing said DNA strands with brominated deoxyuridine triphosphate (BrdUTP) and an enzyme that catalytically attaches the brominated uridine (BrdUrd) of said BrdUTP onto the 3'OH ends of said DNA strands; and
   b. reacting the resulting BrdUrd-DNA strands without denaturation of the DNA with a labeled anti-brominated uridine (anti-BrdUrd) antibody which specifically binds to said BrdUrd.

10. The method of claim 9 wherein said enzyme is selected from the group consisting of terminal deoxynucleotidyl transferase (TdT) and DNA polymerase.

11. The method of claim 9 wherein said anti-brominated uridine (anti-BrdUrd) antibody is selected from the group consisting of fluorescently labeled anti-BrdUrd monoclonal antibody; radiolabeled anti-BrdUrd monoclonal antibody; peroxidase-labeled anti-BrdUrd monoclonal antibody; chromophore labeled anti-BrdUrd monoclonal antibody; fluorescently labeled anti-BrdUrd polyclonal antibody; radiolabeled anti-BrdUrd polyclonal antibody; peroxidase-labeled anti-BrdUrd polyclonal antibody; and chromophore labeled anti-BrdUrd polyclonal antibody.

12. A method for detecting breaks in nuclear DNA strands, within a cell comprising the steps of:
   a. incubating said cell containing said DNA strands with brominated deoxyuridine triphosphate (BrdUTP) and an enzyme that catalytically attaches the brominated uridine (BrdUrd) of said BrdUTP onto the 3'OH ends of said DNA strands;
   b. reacting any resulting BrdUrd-DNA strands with a labeled anti-brominated uridine (anti-BrdUrd) antibody which specifically binds to said BrdUrd; and
   c. detecting said labeled antibody whereby detected cells contain DNA strands having breaks.

13. The method of claim 12 wherein said enzyme is selected from the group consisting of terminal deoxynucleotidyl transferase (TdT) and DNA polymerase.

14. The method of claim 12 wherein said labeled anti-brominated uridine (anti-BrdUrd) antibody is selected from the group consisting of fluorescently labeled anti-BrdUrd monoclonal antibody; radiolabeled anti-BrdUrd monoclonal antibody; peroxidase-labeled anti-BrdUrd monoclonal antibody; chromophore labeled anti-BrdUrd monoclonal antibody; fluorescently labeled anti-BrdUrd polyclonal antibody; radiolabeled anti-BrdUrd polyclonal antibody; peroxidase-labeled anti-BrdUrd polyclonal antibody; and chromophore labeled anti-BrdUrd polyclonal antibody.

15. The method of claim 12 wherein said labeled anti-brominated uridine (anti-BrdUrd) antibody is selected from the group consisting of fluorescently labeled anti-BrdUrd monoclonal antibody and fluorescently labeled anti-BrdU: polyclonal antibody, and said detecting is accomplished by a method selected from the group consisting of flow cytometry, fluorescence microscopy, multiparameter laser scanning microscopy, and visual observation during irradiation with light of an excitation wavelength.

16. The method of claim 12 wherein said labeled anti-brominated uridine (anti-BrdUrd) antibody is selected from the group consisting of radiolabeled anti-BrdUrd monoclonal antibody and radiolabeled anti-BrdUrd polyclonal antibody, and said detecting is accomplished by a method selected from the group consisting of scintillation counting, autoradiography, and Geiger counting.

17. A method for detecting whether cells have undergone apoptosis, comprising the steps of:
   a. fixing said cells;
   b. incubating said cells with brominated deoxyuridine triphosphate (BrdUTP) and an enzyme that catalytically attaches the brominated uridine (BrdUrd) of said BrdUTP onto the 3'OH ends of DNA strands in said cells;
   c. reacting the resulting BrdUrd-DNA strands with a labeled anti-brominated uridine (anti-BrdUrd) antibody which specifically binds to said BrdUrd; and
   d. detecting said labeled antibody, whereby apoptosis is confirmed by the detection of label at a level more than about two standard deviations above the mean level of label found in identically treated control samples known not to have undergone apoptosis.

18. The method of claim 17 wherein said enzyme is selected from the group consisting of terminal deoxynucleotidyl transferase (TdT) and DNA polymerase.

19. The method of claim 17 wherein said labeled anti-brominated uridine (anti-BrdUrd) antibody is selected from the group consisting of fluorescently labeled anti-BrdUrd monoclonal antibody; radiolabeled anti-BrdUrd monoclonal antibody; peroxidase-labeled anti-BrdUrd monoclonal antibody; chromophore labeled anti-BrdUrd monoclonal antibody; fluorescently labeled anti-BrdUrd polyclonal antibody; radiolabeled anti-BrdUrd polyclonal antibody; peroxidase-labeled anti-BrdUrd polyclonal antibody; and chromophore labeled anti-BrdUrd polyclonal antibody.

20. The method of claim 17 wherein said labeled anti-brominated uridine (anti-BrdUrd) antibody is selected from the group consisting of fluorescently labeled anti-BrdUrd monoclonal antibody and fluorescently labeled anti-BrdUrd polyclonal antibody, and said detecting is accomplished by a method selected from the group consisting of flow cytometry, fluorescence microscopy, multiparameter laser scanning microscopy, and visual observation during irradiation with light of an excitation wavelength.

* * * * *